(12) United States Patent
Gharpure et al.

(10) Patent No.: US 10,196,400 B2
(45) Date of Patent: Feb. 5, 2019

(54) PROCESS FOR THE PREPARATION OF LURASIDONE AND ITS INTERMEDIATE

(71) Applicant: PIRAMAL ENTERPRISES LIMITED, Mumbai (IN)

(72) Inventors: Milind Gharpure, Maharashtra (IN); Shashi Kant Tiwari, Pune (IN); Ganesh Wagh, Maharashtra (IN); Galge Revanappa, Maharashtra (IN); Manikrao Warpe, Maharashtra (IN); Yogesh Zalte, Maharashtra (IN); Dhileepkumar Krishnmurthy, Maharashtra (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 15/541,568

(22) PCT Filed: Jan. 5, 2016

(86) PCT No.: PCT/IB2016/050030
§ 371 (c)(1),
(2) Date: Jul. 5, 2017

(87) PCT Pub. No.: WO2016/110798
PCT Pub. Date: Jul. 14, 2016

(65) Prior Publication Data
US 2017/0349601 A1    Dec. 7, 2017

(30) Foreign Application Priority Data
Jan. 8, 2015 (IN) .............. 67/MUM/2015

(51) Int. Cl.
*C07D 487/10* (2006.01)
*C07D 417/12* (2006.01)
*A61P 25/18* (2006.01)

(52) U.S. Cl.
CPC ............ *C07D 487/10* (2013.01); *A61P 25/18* (2018.01); *C07D 417/12* (2013.01)

(58) Field of Classification Search
CPC ........................... C07D 417/12; C07D 487/10
See application file for complete search history.

(56) References Cited

U.S. PATENT DOCUMENTS

2011/0263847 A1    10/2011    Ae et al.

FOREIGN PATENT DOCUMENTS

| CN | 102731512 A | 10/2012 | | |
|---|---|---|---|---|
| CN | 102827157 A | 12/2012 | | |
| CN | 102863437 A | 1/2013 | | |
| CN | 103864774 A | 6/2014 | | |
| WO | 2012/131606 A1 | 10/2012 | | |
| WO | 2013/121440 A1 | 8/2013 | | |
| WO | WO 2013/121440 | * | 8/2013 | .......... C07D 417/12 |
| WO | WO 2014/064714 | * | 5/2014 | |
| WO | 2015/056205 A1 | 4/2015 | | |
| WO | 2015/081920 A1 | 6/2015 | | |

OTHER PUBLICATIONS

Espacenet English abstract of CN 102731512 A.
Espacenet English abstract of CN 102863437 A.
Espacenet English abstract of CN 103864774 A.
Espacenet English abstract of CN 102827157 A.
Indian Patent Application 2306/MUM/2014.

* cited by examiner

*Primary Examiner* — Erich A Leeser
(74) *Attorney, Agent, or Firm* — Ladas & Parry LLP

(57) ABSTRACT

The present invention provides an improved process for preparation of the substantially pure (3aR,7aR)-4'-(benzo[d]isothiazol-3-yl)octahydrospiro[isoindole-2,1'-piperazin]-1'-ium methanesulfonate (referred to as compound-II), which is useful as a key intermediate for the synthesis of lurasidone ((3aR,4S,7R,7aS)-2-{(1R,2R)-2-[4-(1,2-benzisothiazol-3-yl)piperazin-1ylmethyl]cyclohexylmethyl}hexahydro-4,7-methano-2H-isoindole-1,3-dione). The process comprises reaction of the compound-III (as described herein) with the compound-IV (as described herein) in the presence of a solvent mixture selected from an alcohol and water; and a base The improved process for the preparation of compound II provides the product with total amount of unreacted compound-IV as impurity in less than 0.06% and the product with HPLC purity as ≥99.8%. The process further refers purification of Lurasidone hydrochloride, wherein the product contains the residual acetone <5000 ppm.

13 Claims, No Drawings

PROCESS FOR THE PREPARATION OF LURASIDONE AND ITS INTERMEDIATE

RELATED APPLICATION

This application is a national phase entry under 35 USC 371 of International Patent Application No. PCT/IB2016/050030 filed on 05 Jan. 2016, which claims priority from Indian Application No. 67/MUM/2015 filed on 08 Jan. 2015, the disclosures of which are incorporated in their entirety by reference herein.

FIELD OF THE INVENTION

The present invention relates to an improved process for the preparation of (3aR,7aR)-4'-(benzo[d]isothiazol-3-yl) octahydrospiro[isoindole-2,1'-piperazin]-1'-ium methanesulfonate (hereafter referred to as the compound-II), which is useful as a key intermediate for the synthesis of Lurasidone ((3aR,4S,7R,7aS)-2-{(1R,2R)-2-[4-(1,2-benzisothiazol-3-yl)piperazin-1ylmethyl]cyclohexylmethyl}hexahydro-4,7-methano-2H-isoindole-1,3-dione). The process of the present invention further involves transformation of a quaternary ammonium salt (the compound-II) to lurasidone (referred to as the compound-I) and pharmaceutically acceptable salts thereof.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Lurasidone (the Compound-I), is an atypical antipsychotic used in the treatment of schizophrenia and bipolar disorders. The drug is marketed as hydrochloride salt (the compound-I.HCl) by Sunovion Pharms Inc. under the tradename "LATUDA", in the form of oral tablets. Latuda® is indicated for the treatment of patients with schizophrenia. Lurasidone hydrochloride has the chemical name ((3aR,4S,7R,7aS)-2-[((1R,2R)-2-{[4-(1,2-benzisothiazol-3-yl)-piperazin-1-yl]methyl}cyclohexyl)-methyl]hexahydro-1H-4,7-methanisoindol-1,3-dione hydrochloride, and is structurally represented as follows:

Compound-I.HCl

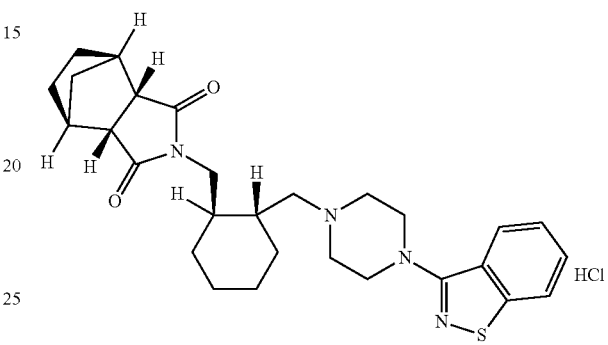

Lurasidone being an important antipsychotic agent, a number of processes for its preparation as well as for its intermediates are known in the art.

U.S. Pat. No. 5,532,372 describe a process for the synthesis of Lurasidone, which is illustrated below in Scheme-I. In the process, the compound, cyclohexane-1,2-diylbis (methylene) dimethanesulfonate (referred to as the compound-III) is reacted with 3-(1-piperazinyl-1,2-benzisothiazole (referred to as the compound-IV) in acetonitrile, and in the presence of sodium carbonate to provide corresponding quaternary ammonium salt as 4'-(benzo[d]isothiazol-3-yl)octahydrospiro[isoindole-2,1'-piperazin]-1'-ium methanesulfonate (the compound-II). The compound-II is further treated with bicyclo[2.2.1]heptane-2-exo-3-exo-dicarboximide in xylene, in the presence of potassium carbonate and dibenzo-18-crown-6-ether to provide lurasidone.

Scheme-I

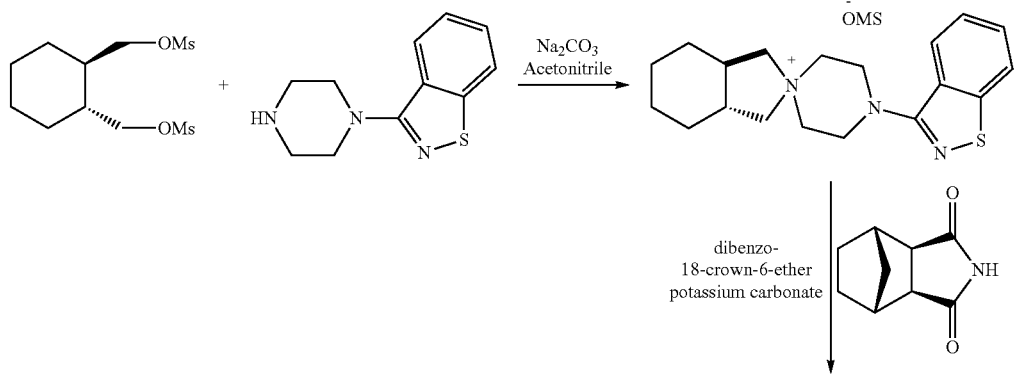

-continued

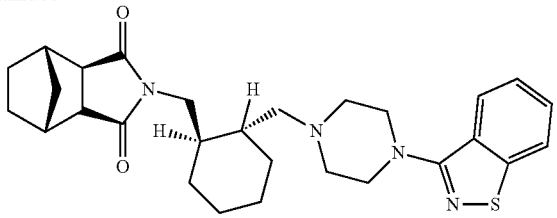

US Published Patent Application 2011/0263848 describes a process for the preparation of the quaternary ammonium salt (the compound-II) which comprises reacting 4-(1,2-benzisothiazol-3-yl)piperazine with (1R,2R)-1,2-bis(methanesulfonyloxymethyl)-cyclohexane in a solvent such as toluene in the presence of a phosphate salt.

Indian Published Patent Application 2306/MUM/2014 ("the IN'2306 Application") describes a process for the synthesis of lurasidone and the intermediates thereof, comprising reacting (R,R) trans 1,2-bis(methane sulphonyl methyl)cyclohexane with 3-(Piperazine-1-yl)benzo[d]isothiazole in presence of a mixture of two or more polar aprotic solvents selected from acetonitrile, N,N-dimethyl formamide (DMF) and/or N,N-dimethyl acetamide (DMAc), and a base at reflux temperature to obtain the quaternary ammonium salt (the compound II), which is then converted to lurasidone. The IN'2306 application demonstrated preparation of the compound II using the solvent combination such as acetonitrile-DMF and acetonitrile-DMAc.

US Published Patent Application 2011/0263847 describes a process for the preparation of the quaternary ammonium salt (the compound-II) comprising reacting 4-(1,2-benziso-thiazol-3-yl)piperazine with (1R,2R)-1,2-bis(methanesulfonyloxymethyl)cyclohexane in a solvent such as toluene, wherein the piperazine compound is used in an excess amount i.e. 1.8 to 15 moles with respect to (1R,2R)-1,2-bis(methanesulfonyloxymethyl)cyclohexane.

Chinese Published Patent Application 102731512 describes a process for the preparation of the quaternary ammonium salt (the compound-II) comprises reaction of 4-(1,2-benzisothiazol-3-yl)piperazine with (1R,2R)-1,2-bis(methanesulfonyloxymethyl)cyclohexane in a solvent such as toluene in the presence of a phase transfer catalyst.

In addition to the afore discussed patent documents, there are a number of patent documents that describe a process for the preparation of the quaternary ammonium salt (the compound-II), the key intermediate for the synthesis of lurasidone. For instance, Published PCT application WO2012/131606 A1, Indian Published patent application 217/MUM/2013, Chinese published patent applications 102863437, 103864774 and 102827157 describe a process for the preparation of the quaternary ammonium salt (compound-II) comprises reaction of 4-(1,2-benzisothiazol-3-yl)piperazine with (1R,2R)-1,2-bis(methanesulfonyloxymethyl)cyclohexane in a solvent or a solvent mixture such as acetonitrile, acetonitrile:water solvent mixture, toluene or DMF, in the presence of a base.

It is evident from the discussion of the processes for the preparation of the quaternary ammonium salt (the compound-II), described in the afore cited patent documents that the reported processes primarily involve use of acetonitrile either as the single solvent or in a mixture of solvents. Acetonitrile is a relatively toxic, and not an environment friendly solvent. Due to its toxic nature, it can cause adverse health effects also. Acetonitrile is covered under Class 2 solvents i.e. solvents to be limited, and residual solvent limit of acetonitrile is 410 ppm in a drug substance as per the ICH (International Conference on Harmonisation) guidelines for residual solvents. Moreover, acetonitrile is a costlier solvent, which renders the process costlier and hence, is not an industrially feasible solvent.

It is also evident from the discussion of the processes described in afore cited patent documents that some of the reported processes involve use of high boiling solvents such as toluene and dimethylformamide as reaction solvent, which subsequently require high reaction temperatures, and this in turn leads to tedious workup procedures. In view of these drawbacks, there is a need to develop an industrially viable commercial process for the preparation of lurasidone and its intermediates; which is simple, efficient and cost-effective process and provides the desired compounds in improved yield and purity.

Inventors of the present invention have developed an improved process that addresses the problems associated with the processes reported in the prior art. The process of the present invention does not involve use of any toxic and/or costly solvents. Moreover, the process does not require additional purification steps and critical workup procedure. Accordingly, the present invention provides a process for the preparation of lurasidone and its intermediates, which is simple, efficient, cost effective, environmentally friendly and commercially scalable for large scale operations.

SUMMARY OF THE INVENTION

In one aspect, the present invention relates to an improved process for the preparation of (3aR,7aR)-4'-(benzo[d]isothiazol-3-yl)octahydrospiro[isoindole-2,1'-piperazin]-1'-ium methanesulfonate (the compound-II), comprising reacting the compound-III (as described herein) with the compound-IV (as described herein) in a mixture of protic solvents; in the presence of a base.

In one aspect, the present invention relates to an improved process for the preparation of (3aR,7aR)-4'-(benzo[d]isothiazol-3-yl)octahydrospiro[isoindole-2,1'-piperazin]-1'-ium methanesulfonate (the compound-II), comprising reacting the compound-III (as described herein) with the compound-IV (as described herein) in a mixture of protic solvents consisting of an alcoholic solvent and water; in the presence of a base.

According to another aspect of the present invention, there is provided an improved process for the preparation of (3aR,7aR)-4'-(benzo[d]isothiazol-3-yl)octahydrospiro[isoindole-2,1'-piperazin]-1'-ium methanesulfonate (the compound-II), wherein the said compound H contains total amount of unreacted compound-IV as impurities of less than 0.06%.

According to another aspect of the present invention, there is provided an improved process for the preparation of (3aR,7aR)-4'-(benzo[d]isothiazol-3-yl)octahydrospiro[isoindole-2,1'-piperazin]-1'-ium methanesulfonate (the compound-II), wherein the said compound II has purity of ≥99%.

According to another aspect of the present invention, there is provided an improved process for the preparation of (3aR,7aR)-4'-(benzo[d]isothiazol-3-yl)octahydrospiro[isoindole-2,1'-piperazin]-1'-ium methanesulfonate (the compound-II), wherein the said compound II is obtained in a yield of about 85-90%.

In another aspect, the present invention relates to an improved process for the purification of Lurasidone and/or its salt, comprising treatment with a solvent mixture of an organic solvent and water.

In another aspect, the present invention relates to an improved process for the purification of Lurasidone hydrochloride, comprising treatment with an alcoholic solvent and water mixture.

In another aspect, the present invention relates to an improved process for the purification of Lurasidone hydrochloride, wherein the product contains the residual acetone of less than 5000 ppm.

DETAILED DESCRIPTION OF THE INVENTION

Accordingly, the present invention relates to an improved process for the preparation of (3aR,7aR)-4'-(benzo[d]isothiazol-3-yl)octahydrospiro[isoindole-2,1'-piperazin]-1'-ium methanesulfonate (the compound II) represented by the following formula, (Compound II)

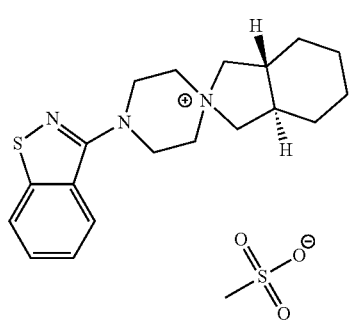

comprising reacting the compound-III represented by the following formula;

Compound -III

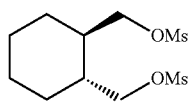

with the compound-IV represented by the following formula;

Compound-IV

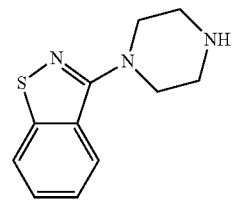

in a mixture of protic solvents; in the presence of a base to obtain the compound II.

The compound-II obtained by the afore described process is optionally, converted into lurasidone free base or a pharmaceutically acceptable salt thereof.

Accordingly, there is provided an improved process for the preparation of lurasidone or a pharmaceutically acceptable salt thereof; comprising the steps of:

(a) preparation of (3aR,7aR)-4'-(benzo[d]isothiazol-3-yl)octahydrospiro[isoindole-2,1'-piperazin]-1'-ium methanesulfonate (the compound II) represented by the following formula;

Compound II

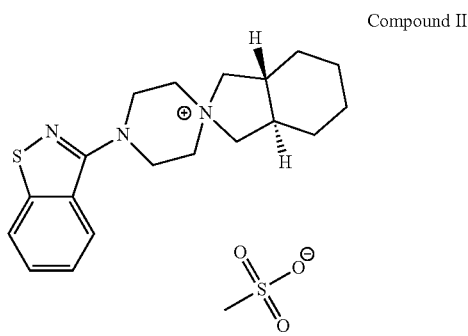

by reacting the compound-III represented by the following formula;

Compound -III

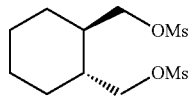

with the compound-IV represented by the following formula;

Compound-IV

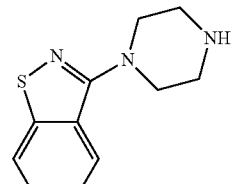

in a mixture of protic solvents consisting of an alcoholic solvent and water; in the presence of a base to obtain the compound II; and (b) converting the compound-II into lurasidone free base or a pharmaceutically acceptable salt thereof.

In the context of the present invention, the term "optionally" when used in reference to any element; including a process step e.g. conversion of a compound; it is intended to mean that the subject element is subsequently converted, or alternatively, is not converted to a further compound. Both alternatives are intended to be within the scope of the present invention.

In the context of the present invention, the term "a mixture of protic solvents" means that the mixture of protic solvents consists of at least two solvents, or more solvents. All alternatives are intended to be within the scope of the present invention.

In an embodiment, the mixture of protic solvents consists of an alcoholic solvent and water.

Accordingly, in an embodiment the present invention relates to a process for the preparation of (3aR,7aR)-4'-(benzo[d]isothiazol-3-yl)octahydrospiro[isoindole-2,1'-piperazin]-1'-ium methanesulfonate (the compound II) represented by the following formula, (Compound II)

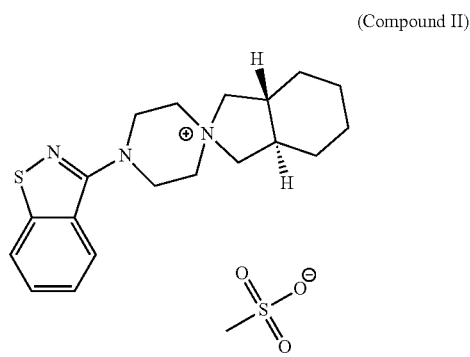

comprising reacting the compound-III represented by the following formula;

Compound -III

with the compound-IV represented by the following formula;

Compound-IV

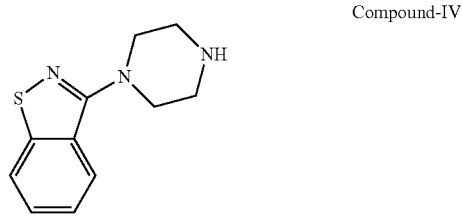 [SMILES: c1ccc2c(N3CCNCC3)nsc2c1]

in the presence of a mixture of protic solvents consisting of an alcoholic solvent and water; in the presence of a base to obtain the compound II;

In an embodiment, the alcoholic solvent contained in the mixture of protic solvents is selected from the group consisting of ethyl alcohol, n-propyl alcohol, isopropyl alcohol, isobutyl alcohol and methanol; or a mixture thereof.

In an embodiment, the alcoholic solvent is isopropyl alcohol (IPA).

In an embodiment, the mixture of protic solvents consists of isopropyl alcohol and water.

In an embodiment, the mixture of protic solvents comprises a mixture of alcoholic solvent and water, wherein the ratio of alcoholic solvent to water ranges from 1:1 to 10:10 as v/v (volume/volume). Preferably, the ratio of the alcoholic solvent to the water ranges from 1:1 to 10:5 as v/v (volume/volume).

In the context of the present invention, the term "ratio" when used with respect to any element e.g. solvent; it is intended to mean that the subject element consists of v/v (volume/volume) ratio ranging from 1:1 to 10:10 of the alcohol to water. All the possible permutation and combination alternatives of v/v ratio are intended to be within the scope of the present invention.

In an embodiment, the mixture of protic solvents comprises an alcoholic solvent and water in the v/v ratio of 3 v:1 v (alcohol:water).

In an embodiment, the solvent mixture of protic solvents comprises isopropyl alcohol (IPA) and water in the v/v ratio of 3 v:1 v (IPA:Water).

In an embodiment, the base is an inorganic base.

In an embodiment, the inorganic base is selected from the group consisting of sodium carbonate, potassium carbonate, sodium bicarbonate, cesium carbonate, calcium carbonate, sodium hydroxide and potassium hydroxide.

In an embodiment, the inorganic base is sodium carbonate.

In a specific embodiment, the process for the preparation of (3aR,7aR)-4'-(benzo[d]isothiazol-3-yl) octahydrospiro[isoindole-2,1'-piperazin]-1'-ium methanesulfonate (the compound-II) comprises the steps of:

(1) dissolving the compound III in an alcohol;
(2) adding the compound IV to the reaction mixture of step (1):
(3) adding a base and water to the reaction mixture of step (2);
(4) stirring the reaction mixture of the above step (3) at a temperature of about 85° C.;
(5) filtering the reaction mixture of the above step (4) at room temperature and evaporating the solvent under vacuum; and
(6) isolating the precipitated product (the compound-II) obtained in the step (5), and washing the compound-II with a solvent at room temperature to obtain the pure compound-II.

The process of the present invention as per the specific embodiment described above is illustrated in the following Scheme-II, Scheme-II

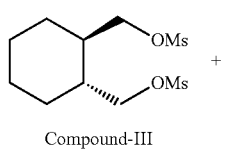

Compound-III

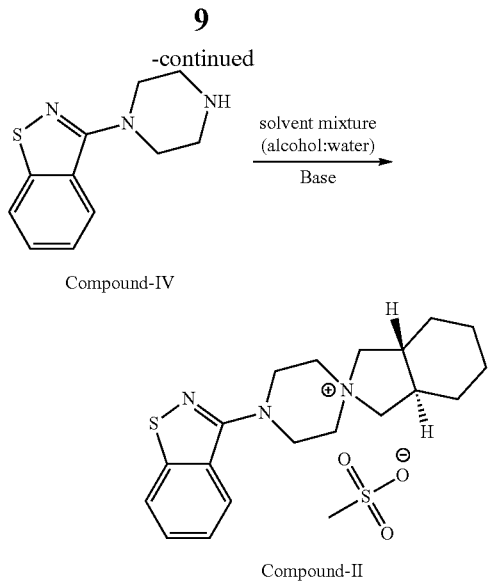

Compound-IV

Compound-II

The process as described above further comprises optionally, converting the pure compound-II into the lurasidone free base or a pharmaceutically acceptable salt thereof.

The alcohol used in the step-(1) of the above process (as depicted in the Scheme II) is selected from the group consisting of ethyl alcohol, n-propyl alcohol, isopropyl alcohol (IPA), isobutyl alcohol and methanol, or a mixture thereof.

In an embodiment, the alcohol used in step-(1) of the above process (as depicted in the Scheme II) is isopropyl alcohol (IPA).

In an embodiment, the base used in the step-(3) of the above process (as depicted in the Scheme II) is an inorganic base.

The inorganic base used in the step-(3) of the above process (as depicted in the Scheme II) is selected from the group consisting of sodium carbonate, potassium carbonate, sodium bicarbonate, cesium carbonate, calcium carbonate, sodium hydroxide and potassium hydroxide.

In an embodiment, the base used in the step (3) is sodium carbonate.

In an embodiment, the quantity of water added in step (3) of the above process (as depicted in the Scheme II) is in the v/v ratio with respect to alcohol solvent ranging from 1:1 to 10:10 as v/v (volume/volume).

In an embodiment, the quantity of water added in step (3) of the above process (as depicted in the Scheme II) is in the v/v ratio with respect to alcohol; and the ratio of alcohol to water is 3 v:1 v (Alcohol:Water).

In an embodiment, the quantity of water added in step (3) of the above process (as depicted in the Scheme II) is in the v/v ratio with respect to isopropyl alcohol (IPA); and the ratio of IPA to water is 3 v:1 v (IPA:Water).

The term 'temperature of about 85° C.' referred to in the step (4) of the above process (as depicted in the Scheme II) can range from 80° C. to 90° C.

The term 'room temperature' referred to in the step (5) and step (6) of the above process (as depicted in the Scheme II) can range from 25° C. to 35° C.

The term 'isolating the precipitated product' referred to in the step (6) corresponds to the steps involving filtration, washing and drying.

The solvent used in the step-(6) of the above process (as depicted in the Scheme II) for the washing of product is selected from an alcohol such as ethyl alcohol, n-propyl alcohol, isopropyl alcohol, isobutyl alcohol and methanol; an ether such as ethyl ether or propyl ether; aromatic hydrocarbon solvents such as toluene, benzene or xylene; and other solvents such as acetone, methyl ethyl ketone, methyl isobutyl ketone, acetonitrile, ethyl acetate, dioxane, tetrahydrofuran, dimethylformamide, dimethyl sulfoxide or dimethylacetamide.

The solvent used in the step-(6) of the above process (as depicted in the Scheme II) for the washing of product is selected from toluene or acetone.

The process of the present invention as illustrated in the above Scheme-II comprises reaction of the compound III with compound IV in the presence of an inorganic base selected from sodium carbonate or potassium carbonate, in a mixture of an alcohol such as isopropyl alcohol (IPA) and water as the solvent, wherein the v/v ratio of isopropyl alcohol with respect to water is 3 v:1 v (IPA:Water). The reaction mixture was heated to a temperature of 80-85° C. for about 24 hours, and filtered at room temperature. The filtrate was distilled out under reduced pressure till visible solid appears. The solid product was washed with toluene and subsequently using acetone. The precipitated product, (3aR,7aR)-4'-(benzo[d]isothiazol-3-yl)octahydrospiro [isoindole-2,1'-piperazin]-1'-ium methanesulfonate (the compound-II) was isolated and the said compound was obtained in a yield of about 85-90% and purity of about ≥99% (HPLC).

The inventors studied the effect of solvent ratio over the yield and purity of compound-II. The Table: 1 consolidates the observations by keeping water as 1 v while varying the IPA volume.

TABLE 1

| Volume of IPA | Volume of water | Yield % compound-II | HPLC purity (%) compound II |
|---|---|---|---|
| 3 v | 1 v | 90.0 | 99.79 |
| 4 v | 1 v | 84.0 | 99.52 |
| 5 v | 1 v | 85.0 | 99.43 |
| 6 v | 1 v | 88.0 | 97.09 |
| 7 v | 1 v | 79.0 | 99.82 |

The inventors also studied the effect of solvent ratio over the yield and purity of compound-II. The Table: 2 consolidate the observations by considering IPA as 3 v while varying the water volume.

TABLE 2

| Volume of IPA | Volume of water | Yield % compound-II | HPLC purity (%) compound II |
|---|---|---|---|
| 3 v | 0.5 v | 53.8 | 63.23 |
| 3 v | 1 v | 90.0 | 99.79 |
| 3 v | 2 v | 87.0 | 99.7 |
| 3 v | 3 v | 67.29 | 99.67 |
| 3 v | 4 v | 66.24 | 99.33 |

The pure product, (3aR,7aR)-4'-(benzo[d]isothiazol-3-yl) octahydrospiro[isoindole-2,1'-piperazin]-1'-ium methanesulfonate (the compound II) was further converted to lurasidone free base or pharmaceutically acceptable salt thereof by a process known in the art, for instance, the process described in U.S. Pat. No. 5,532,372; wherein (3aR,7aR)-4'-(benzo[d]isothiazol-3-yl) octahydrospiro[isoindole-2,1'-piperazin]-1'-ium methanesulfonate (compound II) is reacted with bicyclo[2.2.1]heptane-2-exo-3-exo-dicarboximide.

It is evident from the processes reported in the prior art that the purity of the desired product i.e. the compound-II was about 56.40% (HPLC) with un-reacted compound-IV as impurities in an amount of about 42.46%; whereas the process of the present invention provided the pure desired product, the compound-II in a yield of about 85-90%, purity of about ≥99% (HPLC) with un-reacted compound-IV as impurities in less than 0.06%. This amounts to a significant advantage over the processes reported in the prior art.

In an embodiment, there is provided an improved process for the preparation of (3aR, 7aR)-4'-(benzo[d] isothiazol-3-yl)octahydrospiro[isoindole-2,1'-piperazin]-1'ium methanesulfonate (the compound-II), wherein the compound II contains total amount of un-reacted compound-IV as impurities of less than 0.06%.

In an embodiment, there is provided an improved process for the preparation of (3aR,7aR)-4'-(benzo[d]isothiazol-3-yl)octahydrospiro[isoindole-2,1'-piperazin]-1'-ium methanesulfonate (the compound-II), wherein the compound-II has HPLC purity as ≥99%.

It is further evident from the processes reported in the prior art that the isolation of the pure compound-II involves use of high boiling solvents which subsequently includes high reaction temperature and in turn leads to tedious workup procedures. Also, the processes known in the art involved treatment of the crude compound-II with a solvent and heating to 60-65° C. for several hours, whereas the process of the present invention provided the pure desired product compound-II without harsh purification steps.

In another embodiment, the present invention relates to an improved process for the purification of Lurasidone and/or its salt, comprising treatment with a solvent mixture of an organic solvent and water.

In another embodiment, the present invention relates to an improved process for the purification of Lurasidone hydrochloride, comprising treatment with an alcoholic solvent and water mixture.

In yet another embodiment, the present invention relates to an improved process for the purification of Lurasidone hydrochloride, wherein the product contains the residual acetone <5000 ppm. In an embodiment, the present invention relates to a process for the purification of Lurasidone salt comprising:

(w) preparing a solvent mixture consisting of an organic solvent and water;

(x) adding the Lurasidone salt to the solvent mixture of step (w);

(y) heating the mixture of step (x);

(z) cooling the reaction mixture of step (y) and isolating the precipitated product.

In a specific embodiment, the process for purification of Lurasidone salt comprises the steps of:

(i) adding an organic solvent to the water;

(ii) adding Lurasidone and/or its salt to the stirring solvent mixture of step (i);

(iii) stirring the reaction mixture of the above step (ii) at temperature of about 85° C.;

(iv) cooling the reaction mixture of the above step (iii) at temperature of about 20° C. to 30° C.; and (v) isolating the precipitated product.

The process of the present invention as per the specific embodiment described above is illustrated in the following Scheme-III, Scheme-III

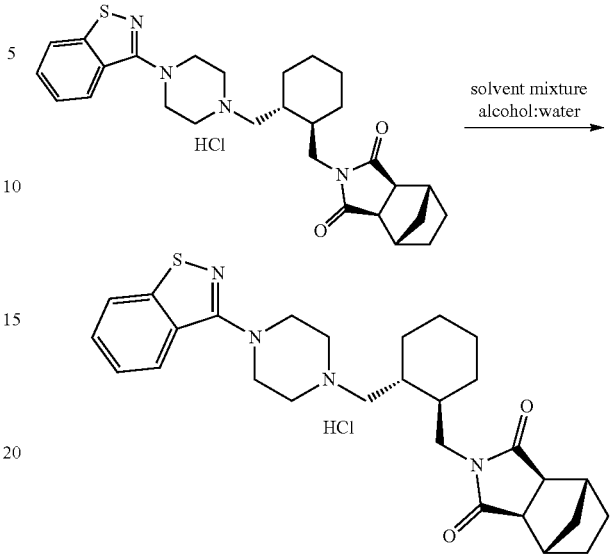

The organic solvent used in the step-(i) of the above process (as depicted in the Scheme III) is selected from the group consisting of alcoholic solvent, halogenated solvent, cyclic solvent, protic solvent, aromatic solvent, ketone, ester, hydrocarbon, nitrile or ether.

In an embodiment, the solvent used in the step-(i) of the above process (as depicted in the Scheme III) is an alcoholic solvent.

The alcoholic solvent used in the step-(i) of the above process (as depicted in the Scheme III) is selected from the group consisting of but not limited to ethyl alcohol, n-propyl alcohol, isopropyl alcohol (IPA), isobutyl alcohol and methanol, or a mixture thereof.

In an embodiment, the alcoholic solvent used in step-(i) of the above process (as depicted in the Scheme III) is isopropyl alcohol (IPA).

The term 'temperature of about 85° C.' referred to in the step (iii) of the above process (as depicted in the Scheme III) can range from 75° C. to 90° C.

The term 'temperature of about 30° C.' referred to in the step (iv) of the above process (as depicted in the Scheme III) can range from 20° C. to 35° C.

The term 'isolating the precipitated product' referred to in the step (v) corresponds to the steps involving filtration, washing and drying.

The process of the present invention as illustrated in the above Scheme-III comprises addition of Lurasidone hydrochloride to the mixture of solvent (IPA:water). The reaction mixture was stirred at temperature of about 85° C. The reaction mixture was cooled to 20-30° C. The precipitated solid filtered as Lurasidone hydrochloride was found to contain residual acetone content <5000 ppm.

The Table: 3 consolidates the observations showing effectively lowering the residual acetone content from Lurasidone hydrochloride by the treatment with alcohol:water solvent system.

TABLE 3

| Compound | Residual Acetone (ppm) Before purification | Residual Acetone (ppm) After purification (IPA: water treatment) |
|---|---|---|
| Lurasidone HCl | 10683 | 2817 |
|  | 5769 | 2 |

In another aspect, the present invention relates to an improved process for the purification of Lurasidone hydrochloride, comprising treatment with an alcoholic solvent and water mixture.

In another aspect, the present invention relates to an improved process for the purification of Lurasidone hydrochloride, wherein the product contains the residual acetone <5000 ppm.

Advantageously, the above identified elements of the process of the instant invention effectively contribute to the reduction of overall cost of the process.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1

Preparation of (3aR,7aR)-4'-(benzo[d]isothiazol-3-yl)octahydrospiro[isoindole-2,1'-piperazin]-1'-ium methanesulfonate (the compound II)

Charged 150.0 mL (3 v) of isopropyl alcohol (IPA) in a flask followed by the addition of the compound-III (50.0 g), 3-(1-Piperazinyl)-1,2-Benzisothiazole (32.84 g), sodium carbonate granular (10.79 g) and water 50 mL (1 v). The reaction mixture was heated at a temperature of 82-85° C. for 24 to 25 h. Cooled the reaction mixture to room temperature, filtered on Buchner funnel and the filtrate was collected.

The filtrate was evaporated under vacuum at 55-65° C. till visible solid appears in the reaction mass. The solid was stirred in 75 mL of toluene at room temperature and the solid was filtered. The wet cake was transferred to a flask and added 125 mL of acetone to it; followed by stirring at room temperature. The resulting solid was filtered to yield the pure title compound (II).

Yield: 63.4 g (90%)
Purity (by HPLC): 99.79%
Unreacted compound-IV as impurity of 0.05%.

Example-2

Preparation of Lurasidone Free Base

Charged 150.0 mL of N,N-dimethylformamide (DMF) in a flask followed by the addition of 50.0 g of the compound-II (as obtained in the above example-1), 19.5 g (3aR,4S,7R,7aS)-4,7-methano-1H-isoindole-1,3(2H)-dione and 19.5 g of potassium carbonate. The reaction mixture was heated at a temperature of about 125° C. for 24 h. The reaction mixture was cooled to room temperature and 400 mL of water was added to it. The reaction mixture was stirred, and the precipitated product was filtered. The wet cake was washed with IPA and Lurasidone free base is obtained as the pure product. [Yield: 46.52 g (80%)]

Example-3

Purification of Lurasidone Hydrochloride

Charged water (200 ml) and IPA (200 ml) in flask followed by the addition of Lurasidone hydrochloride (50 gm, residual acetone: 5769 ppm). The reaction mixture was heated at a temperature of 75-80° C. for about 30 min. The reaction mixture was cooled to 20-30° C. and stirred for about 2 hours. The precipitated solid was filtered and isolated as pure Lurasidone hydrochloride (residual acetone: 2 ppm)

We claim:

1. A process for the preparation of (3aR,7aR)-4'-(benzo[d]isothiazol-3-yl)octahydrospiro[isoindole-2,1'-piperazin]-1'-iummethanesulfonate (II) of the following formula,

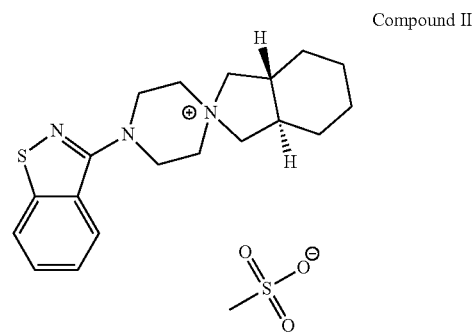

Compound II comprising; reacting the compound-III of the following formula;

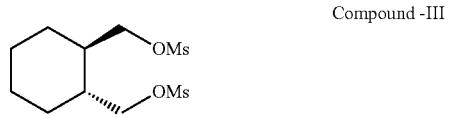 [SMILES: CS(=O)(=O)OC[C@@H]1CCCC[C@H]1COS(C)(=O)=O]

Compound-III with the compound-IV of the following formula;

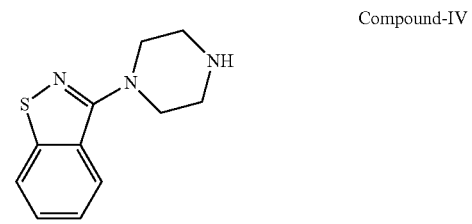 [SMILES: c1ccc2c(N3CCNCC3)nsc2c1]

Compound-IV in a mixture of alcoholic solvent and water and a base; wherein, the obtained compound II contains total amount of unreacted compound-IV as impurities of less than 0.06%.

2. The process according to claim 1, wherein the ratio of alcoholic solvent to water ranges from 1:1 to 10:10 as v/v (volume/volume).

3. The process according to claim 1, wherein the ratio of alcoholic solvent to water ranges from 1:1 to 10:5 as v/v (volume/volume).

4. The process according to claim 1, wherein the solvent mixture comprises isopropyl alcohol (IPA) and water, wherein the ratio of IPA to water is 3:1 v/v (volume/volume).

5. The process according to claim 1, wherein the base is selected from the group consisting of sodium carbonate, potassium carbonate, sodium bicarbonate, cesium carbonate, calcium carbonate, sodium hydroxide and potassium hydroxide.

6. The process according to claim 1, wherein the compound II is obtained in a yield of about 85-90%.

7. The process according to claim 1, wherein the compound II is obtained with a purity of at least 99% (HPLC).

8. The process according to claim 1, wherein the compound II is further converted to Lurasidone free base or a pharmaceutically acceptable salt thereof.

9. The process according to claim 8 wherein the Lurasidone salt is purified by the steps comprising;
(w) preparing a solvent mixture consisting of an alcoholic solvent and water;
x) adding the Lurasidone salt to the solvent mixture of step (w);
(y) heating the mixture of step (x);
(z) cooling the reaction mixture of step (y) and isolating the precipitated product;
wherein the obtained purified Lurasidone salt contains residual acetone of less than 5000 ppm.

10. The process according to claim 9, wherein the alcoholic solvent in step (w) is selected from ethyl alcohol, n-propyl alcohol, isopropyl alcohol (IPA), isobutyl alcohol or methanol, or a mixture thereof.

11. The process according to claim 9, wherein the heating temperature in step (y) ranges from 75° C. to 90° C.

12. The process according to claim 9, wherein the cooling temperature in step (z) ranges from 20° C. to 35° C.

13. The process according to claim 8, wherein the Lurasidone salt is Lurasidone hydrochloride, which is purified by the steps comprising;
(i) preparing a solvent mixture of isopropyl alcohol (IPA) and water;
(ii) adding the Lurasidone hydrochloride to the solvent mixture of step (i);
(iii) heating the mixture of step (ii) to a temperature of about 85° C.;
(iv) cooling the reaction mixture of step (iii) to a temperature of about 20-30° C.; and
(v) isolating the precipitated product;
wherein the obtained purified Lurasidone hydrochloride contains residual acetone of less than 5000 ppm.

* * * * *